(12) United States Patent
Kuehnert et al.

(10) Patent No.: US 7,541,495 B2
(45) Date of Patent: Jun. 2, 2009

(54) PARA-ALKYL-SUBSTITUTED N-(4-HYDROXY-3-METHOXY-BENZYL)-CINNAMAMIDES, PHARMACEUTICAL COMPOSITIONS AND USES THEREOF

(75) Inventors: Sven Kuehnert, Dueren (DE); Robert Frank, Aachen (DE); Ruth Jostock, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/705,004

(22) Filed: Feb. 12, 2007

(65) Prior Publication Data

US 2007/0208083 A1 Sep. 6, 2007

Related U.S. Application Data

(63) Continuation of application No. PCT/EP2005/053898, filed on Aug. 8, 2005.

(30) Foreign Application Priority Data

Aug. 12, 2004  (DE) .................. 10 2004 039 373

(51) Int. Cl.
  *C07C 233/09* (2006.01)
  *C07C 231/02* (2006.01)
  *A61K 31/16* (2006.01)

(52) U.S. Cl. ...................... 564/182; 514/616
(58) Field of Classification Search ................ 564/182, 564/139; 514/616
See application file for complete search history.

(56) References Cited

FOREIGN PATENT DOCUMENTS

| | | | |
|---|---|---|---|
| WO | WO 91/16892 A1 | 11/1991 | |
| WO | WO 97/45400 A1 | 12/1997 | |
| WO | WO 02/076946 A2 | 10/2002 | |
| WO | WO 03/092676 A1 | 11/2003 | |

OTHER PUBLICATIONS

T. Wayne Schultz et al., "Structure-Activity Relationships for Osteolathyrism: II. Effects of Alkyl-Substituted Acid Hydrazides", Toxicology 53, (1988) pp. 147-159, Elsevier Scientific Publishers Ireland Ltd.
T. Sudhakar Johnson et al., "Precursor Biotransformation in Immobilized Placental Tissues of Capsicum frutescens Mill.:II. Influence of Feeding Intermediates . . . ", J. Plant Physiol., (1998) pp. 240-243, vol. 153.
Antonio Ferrer-Montiel et al., "Molecular architecture of the vanilloid receptor insights for drug design", Eur. J. Biochem. 271, (2004), pp. 1820-1826.
Christopher S.J. Walpole et al., "Analogues of Capsaicin with Agonist Activity as Novel Analgesic Agents; Structure-Activity Studies. 3. The Hydrophobic Side-Chain C-Region", J. Med. Chem. 1993, 36, pp. 2381-2389.
Arpad Szallasi et al., "Vanilloid (Capsaicin) Receptors and Mechanisms", The American Society for Pharmacology and Experimental Therapeutics, Pharmacological Reviews, 1999, vol. 51, No. 2, pp. 159-211.
Form PCT/IPEA/409 w/English translation (Eleven (11) pages).
International Search Report dated Dec. 5, 2005 w/English translation of pertinent portion (Two (2) pages).
German Search Report dated Jan. 19, 2005 w/English translation of pertinent portion (Eight (8) pages).

*Primary Examiner*—Shailendra Kumar
(74) *Attorney, Agent, or Firm*—Crowell & Moring LLP

(57) ABSTRACT para-Alkyl-substituted N-(4-hydroxy-3-methoxybenzyl)-cinnamic acid amide compounds, processes for the preparation thereof, pharmaceutical compositions containing these compounds, and the use of these compounds for treating or inhibiting specific diseases or disorders.

13 Claims, No Drawings

PARA-ALKYL-SUBSTITUTED N-(4-HYDROXY-3-METHOXY-BENZYL)-CINNAMAMIDES, PHARMACEUTICAL COMPOSITIONS AND USES THEREOF

CROSS REFERENCE TO RELATED APPLICATIONS

This application is a continuation of international patent application no. PCT/EP2005/053898, filed Aug. 8, 2005 designating the United States of America and published in German on Feb. 13, 2006 as WO 2006/018406, the entire disclosure of which is incorporated herein by reference. Priority is claimed based on Federal Republic of Germany patent application no. DE 10 2004 039 373.7, filed Aug. 12, 2004.

BACKGROUND OF THE INVENTION

The present invention relates to para-alkyl-substituted N-(4-hydroxy-3-methoxybenzyl)-cinnamic acid amides, to processes for the preparation thereof, to medicinal drugs containing these compounds, and to the use of these compounds for the preparation of medicinal drugs.

The treatment of pain, especially of neuropathic pain, is of great importance in the field of medicine. There is a worldwide need for effective therapies for pain. The urgent need for attaining patient-friendly, target-orientated treatment of chronic and non-chronic states of pain, by which is to be understood the successful and satisfactory treatment of pain in the patient, is also documented by the large number of scientific papers which have recently appeared in the field of applied analgesics and basic research on nociception.

A suitable approach to the treatment of pain, especially pain selected from the group consisting of acute pain, chronic pain, neuropathic pain, and visceral pain, preferably neuropathic pain, is the vanilloid receptor subtype 1 (VR1/TRPV1), which is frequently referred to as the capsaicin receptor. This receptor is stimulated inter alia by vanilloids such as, for example, capsaicin, heat, and protons and plays a central role in causing pain. Moreover, it is important for a large number of other physiological and pathophysiological processes, such as, for example, migraine; depression; neurodegenerative diseases; cognitive disorders; anxiety; epilepsy; coughing; diarrhoea; pruritus; motor neurone diseases; disorders of the cardiovascular system; disorders of food intake; medicinal drug dependency; medicinal drug abuse; and especially urinary incontinence.

SUMMARY OF THE INVENTION

One object of the present invention is, therefore, to provide novel compounds which are particularly well-suited as pharmacologically active ingredients in medicinal drugs, especially in medicinal drugs for the treatment of disorders or diseases that are mediated at least partly by vanilloid receptors 1 (VR1/TRPV1 receptors).

Another object of the invention is to provide a new method of treating or inhibiting disorders or diseases that are mediated at least partly by vanilloid receptors 1 (VR1/TRPV1 receptors).

Surprisingly, it has now been found that the para-alkyl-substituted N-(4-hydroxy-3-methoxy-benzyl)-cinnamic acid amides of formulas I and Ia below exhibit excellent affinity for the vanilloid receptor subtype 1 (VR1/TRPV1 receptor) and are therefore particularly well-suited for the inhibition and/or treatment of disorders or diseases that are mediated at least partly by vanilloid receptors 1 (VR1/TRPV1).

The compounds according to the invention are particularly suitable for the treatment and/or inhibition of pain, especially pain selected from the group consisting of acute pain, chronic pain, neuropathic pain, and visceral pain; arthralgia; migraine; depression; nervous disorders; neurotrauma; neurodegenerative diseases, especially those selected from the group consisting of multiple sclerosis, Alzheimer's disease, Parkinson's disease, and Huntington's disease; cognitive disorders, preferably cognitive deficiencies, more preferably memory disorders; anxiety; epilepsy; respiratory tract diseases, preferably selected from the group consisting of asthma and pneumonia; coughing; urinary incontinence; an overactive bladder (OAB); diarrhoea; gastric ulcers; colitis syndrome; cerebral apoplexy; irritation of the eyes; cutaneous irritation; neurotic skin diseases; inflammatory diseases, preferably inflammation of the colon; pruritus; disorders of food intake, particularly those selected from the group consisting of bulimia, cachexia, anorexia, and obesity; medicinal drug dependency; medicinal drug abuse; withdrawal symptoms following medicinal drug dependency; development of immunity to medicinal drugs, preferably to natural or synthetic opioids; drug dependency; drug abuse; withdrawal symptoms following drug dependency; alcohol dependency; alcohol abuse; withdrawal symptoms following alcohol dependency; for diuresis; for antinatriuresis; for influencing the cardiovascular system; for increasing vigilance; for increasing libido; for modulating motor activity; or for local anaesthesia.

The present invention accordingly provides para-alkyl-substituted N-(4-hydroxy-3-methoxybenzyl)-cinnamic acid amides of formula I

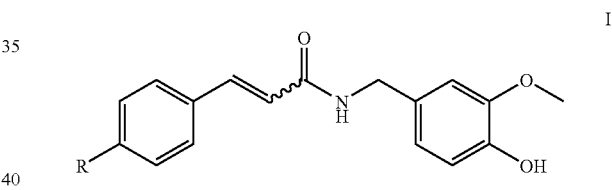

wherein R represents a linear or branched alkyl group, in each case optionally in the form of pure isomers thereof or in the form of a mixture of isomers in any desired mixing ratio, or in each case in the form of appropriate salts, or in each case in the form of appropriate solvates.

Persons skilled in the art will understand that, in the compounds of formula I according to the invention, the substituents on the double bond of the para-alkyl-substituted N-(4-hydroxy-3-methoxy-benzyl)-cinnamic acid amides that are other than hydrogen may have either the cis or the trans configuration relative to one another. The corresponding trans isomer is frequently also referred to as the (E) isomer and the cis isomer as the (Z) isomer.

Preferred are para-alkyl-substituted trans-N-(4-hydroxy-3-methoxybenzyl)-cinnamic acid amides of formula Ia

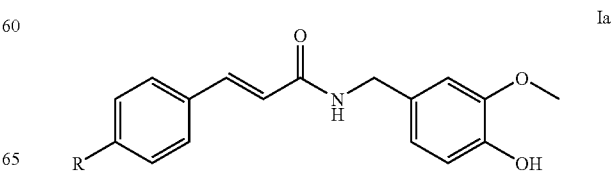

wherein R represents a linear or branched alkyl group, in each case optionally in the form of the pure isomers thereof or in the form of a mixture of isomers in any desired mixing ratio, or in each case in the form of appropriate salts, or in each case in the form of appropriate solvates.

Preference is also given to compounds of formulas I and Ia in which R represents a linear or branched $C_{1-20}$ alkyl group; more preferably a linear or branched $C_{1-10}$ alkyl group; even more preferably an alkyl group selected from the group consisting of methyl, ethyl, n-propyl, isopropyl, n-butyl, isobutyl, sec.-butyl, tert.-butyl, n-pentyl, 2-pentyl, 3-pentyl, isopentyl, neopentyl, 1,1-dimethylpropyl, 1,2-dimethylpropyl, n-hexyl, 2-hexyl, 3-hexyl, isohexyl, neohexyl, n-heptyl, 2-heptyl, 3-heptyl, 4-heptyl, isoheptyl, neoheptyl, n-octyl, 2-octyl, 3-octyl, 4-octyl, isooctyl, neooctyl, n-nonyl, 2-nonyl, 3-nonyl, 4-nonyl, 5-nonyl, isononyl, neononyl and n-decyl; and most preferably an alkyl group selected from the group consisting of methyl, ethyl, n-propyl, isopropyl, n-butyl, isobutyl, tert.-butyl, neopentyl and n-octyl.

Particular preference is given to the compounds of formulas I and Ia selected from the group consisting of:

[1] para-methyl-trans-N-(4-hydroxy-3-methoxybenzyl)-cinnamic acid amide,
[2] para-ethyl-trans-N-(4-hydroxy-3-methoxybenzyl)-cinnamic acid amide,
[3] para-isopropyl-trans-N-(4-hydroxy-3-methoxybenzyl)-cinnamic acid amide and
[4] para-tert.-butyl-trans-N-(4-hydroxy-3-methoxybenzyl)-cinnamic acid amide,
[5] para-propyl-trans-N-(hydroxy-3-methoxybenzyl)-cinnamic acid amide,
[6] para-isobutyl-trans-N-(4-hydroxy-3-methoxybenzyl)-cinnamic acid amide,
[7] para-neopentyl-trans-N-(4-hydroxy-3-methoxybenzyl)-cinnamic acid amide,
[8] para-butyl-trans-N-(4-hydroxy-3-methoxybenzyl)-cinnamic acid amide; and
[9] para-octyl-trans-N-(4-hydroxy-3-methoxybenzyl)-cinnamic acid amide;

and the respective salts and solvates thereof.

The compound para-tert.-butyl-trans-N-(4-hydroxy-3-methoxybenzyl)-cinnamic acid amide and salts and solvates thereof are especially preferred.

When the compounds of formulas I and Ia according to the invention are in the form of their salts, the salts can preferably be selected from the group consisting of the alkali metal salts, preferably the sodium or potassium salts. Also preferred are salts with cations of formula $[NR_xH_{4-x}]^+$, wherein R represents a linear or optionally branched alkyl group having from 1 to 4 carbon atoms and x represents 0, 1, 2, 3 or 4. The above-mentioned salts may also be present in the form of appropriate solvates, preferably in the form of the hydrates.

The present invention further provides a process for preparing the compounds according to the invention of the above formulas I and Ia, in which process at least one aldehyde of formula II

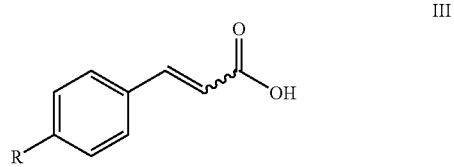

wherein R has the meanings stated above, is caused to react with malonic acid (OH—C(=O)—CH$_2$—C(=O)—OH), optionally in a reaction medium, in the presence of at least one base, the resulting para-alkyl-substituted cinnamic acid of formula III

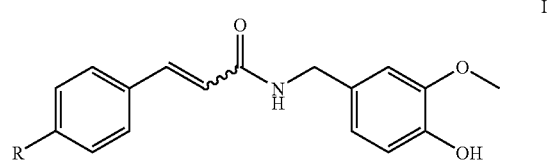

wherein R has the meaning given above, optionally in the form of an appropriate salt, is optionally isolated and optionally purified and is caused to react with 4-hydroxy-3-methoxybenzylamine, optionally in the form of an appropriate salt, preferably in the form of the hydrochloride, in a reaction medium, optionally in the presence of at least one base, optionally in the presence of at least one suitable coupling agent, to form a corresponding compound of formula I optionally in the form of a corresponding salt, wherein R has the meanings stated above, which compound is optionally purified and optionally isolated.

The process according to the invention for the preparation of para-alkyl-substituted N-(4-hydroxy-3-methoxybenzyl)-cinnamic acid amides is also shown in the following Scheme 1:

Scheme 1

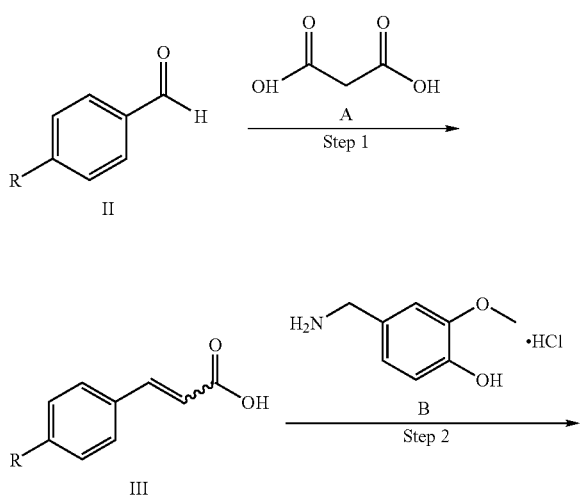

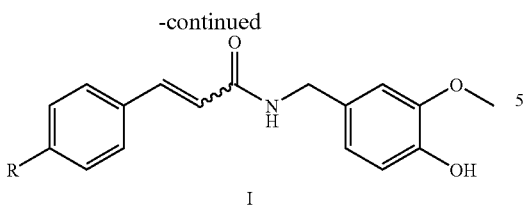

In the first step of Scheme 1, aldehydes of the above formula II wherein R has the meanings stated above are caused to react with malonic acid (compound A), optionally in a suitable reaction medium preferably selected from the group consisting of tetrahydrofuran, dimethylformamide, dimethylacetamide, acetonitrile, pyridine, dimethyl sulfoxide, xylene, toluene, and mixtures of at least two of the above-mentioned reaction media, optionally in the presence of at least one base, preferably in the presence of an organic base selected from the group consisting of piperidine, pyridine, dimethylaminopyridine, triethylamine, and diisopropylethylamine, preferably at temperatures ranging from 20° C. to 150° C., more preferably at temperatures ranging from 60° C. to 120° C., to form para-alkyl-substituted cinnamic acids of formula III wherein R has the meanings stated above, optionally in the form of an appropriate salt, which acids are optionally isolated and optionally purified. It is particularly preferred to carry out the reaction in pyridine in the presence of piperidine.

In the second step, compounds of the above formula III are caused to react, preferably at temperatures ranging from −70° C. to 100° C., with 4-hydroxy-3-methoxybenzylamine, optionally in the form of an appropriate salt, preferably in the form of the hydrochloride (compound B), in a reaction medium preferably selected from the group consisting of diethyl ether, tetrahydrofuran, acetonitrile, methanol, ethanol, dimethylformamide, dichloromethane, and a mixture of at least two of the above-mentioned reaction media, optionally in the presence of at least one suitable coupling agent preferably selected from the group consisting of 1-benzotriazolyloxy-tris(dimethylamino)-phosphonium hexafluorophosphate (BOP), dicyclohexyl-carbodiimide (DCC), N'-(3-dimethylaminopropyl)-N-ethylcarbodiimide (EDCI), 1,1-carbonyldiimadazole (CDI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethylronium hexafluorophosphate (HBTU), O-(benzotriazol-1-yl)-N,N,N',N'-tetramethylronium tetrafluoroborate (TBTO), and 1-hydroxy-7-azabenzotriazole (HOAt), optionally in the presence of at least one organic base preferably selected from the group consisting of triethylamine, piperidine, N-methylmorpholine, pyridine, dimethylaminopyridine, and diisopropylethylamine at temperatures ranging from −70° C. to 100° C. to form compounds of formula I, optionally in the form of an appropriate salt, preferably in the form of the corresponding hydrochloride, which compounds are optionally purified and optionally isolated.

The para-alkyl-substituted cinnamic acid of formula III obtained by the process according to the invention is usually in the form of a mixture of its cis/trans isomers, from which the respective isomer, especially the trans isomer of formula IIIa

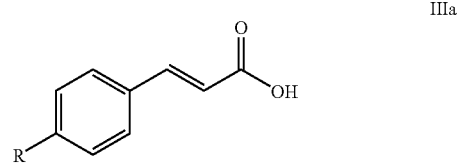

can be isolated by conventional methods known to persons skilled in the art and can optionally be purified. Examples which may be mentioned include chromatographic separation processes, particularly liquid chromatography processes under standard pressure or under elevated pressure, preferably MPLC and HPLC processes, or recrystallization from a suitable solvent, preferably from methanol. The para-alkyl-substituted cinnamic acid of formula IIIa can likewise be used in step 2 of the process according to the invention according to Scheme 1.

When the para-alkyl-substituted N-(4-hydroxy-3-methoxybenzyl)-cinnamic acid amides obtained by the process according to the invention are in the form of a mixture of their cis/trans isomers, the trans isomer of formula Ia

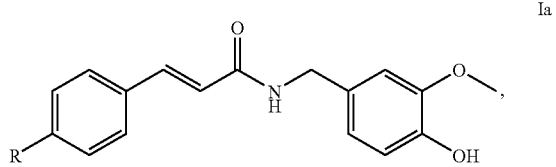

can be isolated therefrom by conventional methods known to persons skilled in the art and can optionally be purified. Examples which may be mentioned include chromatographic separation processes, especially liquid chromatography processes under standard pressure or under elevated pressure, preferably MPLC and HPLC processes, or recrystallisation from a suitable solvent.

The compounds of formula II above and the compounds A and B are each commercially available and/or can be prepared by the conventional processes known to persons skilled in the art.

The reactions described above can each be carried out under the conventional conditions known to persons skilled in the art, for example with regard to the pressure or the order of addition of the components. Where appropriate, the optimal procedure for the particular conditions can be determined by those skilled in the art by simple preliminary experiments.

The intermediates and end products obtained by the reactions described above may, if desired and/or necessary, be purified and/or isolated by conventional methods known to persons skilled in the art. Suitable purification processes are, for example, extraction processes and chromatographic processes such as column chromatography or preparative chromatography.

All of the above-described process steps, and the respective purification and/or isolation of intermediates or end products may be carried out entirely or partially under an inert gas atmosphere, preferably under a blanket of nitrogen.

If, after their preparation, the para-alkyl-substituted N-(4-hydroxy-3-methoxybenzyl)-cinnamic acid amides of the above formulas I and Ia are obtained in the form of a mixture of isomers, these can be separated by conventional processes known to persons skilled in the art and optionally isolated. Examples which may be mentioned include chromatographic separation processes on chiral phase, particularly liquid chromatography processes under standard pressure or under elevated pressure, preferably MPLC and HPLC processes.

The para-alkyl-substituted N-(4-hydroxy-3-methoxybenzyl)-cinnamic acid amides according to the invention of the above formulas I and Ia and, optionally, corresponding isomers can be obtained in the form of appropriate salts, especially in the form of appropriate physiologically acceptable salts, by means of conventional processes known to persons skilled in the art, while it is possible for the medicinal drug according to the invention to contain one or more salts of one or more of these compounds.

The para-alkyl-substituted N-(4-hydroxy-3-methoxybenzyl)-cinnamic acid amides according to the invention of the above formulas I and Ia and, optionally, corresponding isomers, and in each case their physiologically acceptable salts, can alternatively be obtained in the form of their solvates, especially in the form of their hydrates, by means of conventional processes known to persons skilled in the art.

It has been found, surprisingly, that the para-alkyl-substituted N-(4-hydroxy-3-methoxybenzyl)-cinnamic acid amides according to the invention of the above formulas I and Ia are suitable for vanilloid receptor 1 (VR1/TRPV1) regulation, especially as agonists for vanilloid receptor 1 (VR1/TRPV1) activation, and can therefore be used, in particular, as pharmaceutically active ingredients in medicinal drugs for the inhibition and/or treatment of disorders or diseases associated with these receptors or processes. The para-alkyl-substituted N-(4-hydroxy-3-methoxybenzyl)-cinnamic acid amides according to the invention of the above formulas I and Ia and, optionally, appropriate isomers, and in each case the appropriate salts and solvates, are toxicologically harmless and are therefore suitable as pharmaceutically active ingredients in medicinal drugs.

The present invention accordingly further provides a pharmaceutical composition comprising at least one para-alkyl-substituted N-(4-hydroxy-3-methoxybenzyl)-cinnamic acid amide according to the invention of the above formula I or Ia, in each case optionally in the form of one of its pure isomers or in the form of a mixture of isomers in any desired mixing ratio, or in each case in the form of appropriate salts, or in each case in the form of appropriate solvates, and optionally one or more pharmaceutically acceptable adjuvants.

The pharmaceutical composition according to the invention is suitable for vanilloid receptor 1 (VR1/TRPV1) regulation, especially for vanilloid receptor 1 (VR1/TRPV1) activation. The pharmaceutical composition drug according to the invention is therefore preferably suitable for the inhibition and/or treatment of disorders and/or diseases that are mediated at least partly by vanilloid receptors 1 (VR1/TRPV1).

The pharmaceutical composition according to the invention is preferably suitable for the inhibition and/or treatment pain, especially of pain selected from the group consisting of acute pain, chronic pain, neuropathic pain, and visceral pain; arthralgia; migraine; depression; nervous disorders; neurotrauma; neurodegenerative diseases, more preferably selected from the group consisting of multiple sclerosis, Alzheimer's disease, Parkinson's disease, and Huntington's disease; cognitive disorders, more preferably cognitive deficiencies, very preferably memory disorders; anxiety; epilepsy; respiratory tract diseases, preferably selected from the group consisting of asthma and pneumonia; coughing; urinary incontinence; an overactive bladder (OAB); gastric ulcers; colitis syndrome; cerebral apoplexy; irritation of the eyes; cutaneous irritation; neurotic skin diseases; inflammatory diseases, preferably inflammation of the colon; diarrhoea; pruritus; disorders of food intake, more preferably selected from the group consisting of bulimia, cachexia, anorexia and obesity; medicinal drug dependency; medicinal drug abuse; withdrawal symptoms following medicinal drug dependency; development of immunity to medicinal drugs, more preferably to natural or synthetic opioids; drug dependency; drug abuse; withdrawal symptoms following drug dependency; alcohol dependency; alcohol abuse; withdrawal symptoms following alcohol dependency; for diuresis; for antinatriuresis; for influencing the cardiovascular system; for increasing vigilance; for increasing libido; for modulating motor activity; or for local anaesthesia.

The pharmaceutical composition according to the invention is particularly suitable for the inhibition and/or treatment of urinary incontinence or pain, particularly pain selected from the group consisting of acute pain, chronic pain, neuropathic pain, and visceral pain, and is especially well-suited for the inhibition and/or treatment of pain, particularly of pain selected from the group consisting of acute pain, chronic pain, neuropathic pain, and visceral pain.

The present invention further relates to the use of at least one para-alkyl-substituted N-(4-hydroxy-3-methoxybenzyl)-cinnamic acid amide according to the invention of the above formula I or Ia, in each case optionally in the form of one of its pure isomers or in the form of a mixture of isomers in any desired mixing ratio, or in each case in the form of appropriate salts, or in each case in the form of appropriate solvates, and optionally one or more pharmaceutically acceptable adjuvants, in the preparation of a medicinal drug for vanilloid receptor 1 (VR1/TRPV1) regulation, particularly for vanilloid receptor 1 (VR1/TRPV1) activation.

Preference is given to the use of at least one para-alkyl-substituted N-(4-hydroxy-3-methoxybenzyl)-cinnamic acid amide according to the invention of the above formula I or Ia, in each case optionally in the form of one of its pure isomers or in the form of a mixture of isomers in any desired mixing ratio, or in each case in the form of appropriate salts, or in each case in the form of appropriate solvates, and optionally one or more pharmaceutically acceptable adjuvants, in the preparation of a medicinal drug for the inhibition and/or treatment of disorders and/or diseases that are mediated at least partly by vanilloid receptors 1 (VR1/TRPV1).

Particular preference is also given to the use of at least one para-alkyl-substituted N-(4-hydroxy-3-methoxybenzyl)-cinnamic acid amide according to the invention of the above formula I or Ia, in each case optionally in the form of one of its pure isomers or in the form of a mixture of isomers in any desired mixing ratio, or in each case in the form of appropriate salts, or in each case in the form of appropriate solvates, and optionally one or more pharmaceutically acceptable adjuvants, in the preparation of a medicinal drug for the inhibition and/or treatment of pain, more preferably pain selected from the group consisting of acute pain, chronic pain, neuropathic pain, and visceral pain; arthralgia; migraine; depression; nervous disorders; neurotrauma; neurodegenerative diseases, more preferably selected from the group consisting of multiple sclerosis, Alzheimer's disease, Parkinson's disease, and Huntington's disease; cognitive disorders, more preferably cognitive deficiencies, very preferably memory disorders; anxiety; epilepsy; respiratory tract diseases, preferably selected from the group consisting of asthma and pneumonia; coughing; urinary incontinence; an overactive bladder (OAB); diarrhoea; gastric ulcers; colitis syndrome; cerebral apoplexy; irritation of the eyes; cutaneous irritation; neurotic skin diseases; inflammatory diseases, preferably inflammation of the colon; pruritus; disorders of food intake, more preferably selected from the group consisting of bulimia, cachexia, anorexia, and obesity; medicinal drug dependency; medicinal drug abuse; withdrawal symptoms following medicinal drug dependency; development of immunity to medicaments, more preferably to natural or synthetic opioids; drug dependency; drug abuse; withdrawal symptoms following drug dependency; alcohol dependency; alcohol abuse; withdrawal symptoms following alcohol dependency; for diuresis; for antinatriuresis; for influencing the cardiovascular system; for increasing vigilance; for increasing libido; for modulating motor activity; or for local anaesthesia, preferably for the inhibition and/or treatment of urinary incontinence or pain, particularly pain selected from the group consisting of acute pain, chronic pain, neuropathic pain, and visceral pain, more preferably for the inhibition and/or treatment of pain, particularly pain selected from the group consisting of acute pain, chronic pain, neuropathic pain, and visceral pain.

The pharmaceutical composition according to the invention is suitable for administration to adults and to children, including infants and babies.

The pharmaceutical composition according to the invention may exist in the form of a liquid, semi-solid, or solid medicament form, for example in the form of injection solutions, drops, juices, syrups, sprays, suspensions, tablets, patches, capsules, plasters, suppositories, ointments, creams, lotions, gels, emulsions, aerosols, or in multiparticulate form, for example in the form of pellets or granules, optionally compressed to tablets, filled into capsules or suspended in a liquid, and may also be administered as such.

In addition to at least one para-alkyl-substituted N-(4-hydroxy-3-methoxybenzyl)-cinnamic acid amide according to the invention of the above formula I or Ia, in each case optionally in the form of one of its pure isomers or in the form of a mixture of isomers in any desired mixing ratio, or in each case in the form of appropriate salts, or in each case in the form of appropriate solvates, the pharmaceutical composition according to the invention usually comprises further physiologically acceptable pharmaceutical adjuvants which can preferably be selected from the group consisting of carriers, fillers, solvents, diluents, surface-active substances, colorants, preservatives, disintegrators, glidants, lubricants, flavorings, and binders.

The choice of physiologically acceptable adjuvants and the amounts thereof to be used are dependent on whether the pharmaceutical composition is to be administered orally, subcutaneously, parenterally, intravenously, intraperitoneally, intradermally, intramuscularly, intranasally, buccally, rectally, or locally, for example on infections of the skin, the mucous membranes, or the eyes. Formulations in the form of tablets, dragees, capsules, granules, pellets, drops, juices, and syrups are preferably suitable for oral administration; whilst solutions, suspensions, readily reconstitutable dry formulations, and sprays are suitable for parenteral and topical administration and for administration by inhalation.

The para-alkyl-substituted N-(4-hydroxy-3-methoxybenzyl)-cinnamic acid amides of the above formulas I and Ia that are used in the pharmaceutical composition according to the invention in a depot, in dissolved form, or in a plaster, optionally with the addition of agents which promote penetration of the skin, are suitable formulations for percutaneous administration.

Preparation forms which can be used orally or percutaneously are also capable of affording delayed release of the respective para-alkyl-substituted N-(4-hydroxy-3-methoxybenzyl)-cinnamic acid amides of the above formulas I and Ia.

The preparation of the pharmaceutical according to the invention is carried out using conventional agents, devices, methods, and processes known from the prior art, as are described, for example, in "Remington's Pharmaceutical Sciences", ed. A. R. Gennaro, 17th Edition, Mack Publishing Company, Easton, Pa., 1985, especially in Part 8, Chapters 76 to 93. The relevant description is incorporated herein by reference and is to be regarded as part of the disclosure.

The amount of the respective para-alkyl-substituted N-(4-hydroxy-3-methoxybenzyl)-cinnamic acid amide of the above formula I or Ia to be administered to the patients can vary and is dependent, for example, on the weight or age of the patient, the mode of administration, and on the indication and the severity of the disease. From 0.005 to 5000 mg/kg, preferably from 0.05 to 500 mg/kg of body weight of the patient of at least one such compound are usually administered.

Pharmacological Methods:

1. Functional Study on the Vanilloid Receptor 1 (VR1/TRPV1 Receptor)

The agonist activity or antagonist activity of the substances to be tested on the vanilloid receptor 1 (VR1/TRPV1) of the species human and rat can be determined using the following assay. According to this assay, the $Ca^{2+}$ influx through the channel is quantified by means of a $Ca^{2+}$-sensitive dye (type Fluo-4, Molecular Probes Europe BV, Leiden, Netherlands) in the Fluorescent Imaging Plate Reader (FLIPR, Molecular Devices, Sunnyvale, USA).

Procedure:

Chinese hamster ovary cells (CHO K1 cells, European Collection of Cell Cultures (ECACC), England) are stably transfected with the human or rat vanilloid receptor 1 (VR1) gene. For functional studies, these cells are plated out in a density of 25,000 cells/well on poly-D-lysine-coated, black 96-well plates having a clear base (BD Biosciences, Heidelberg, Germany). The cells are incubated overnight at 37° C. and 5% $CO_2$ in culture medium (Nutrient Mixture Ham's F12, Gibco Invitrogen GmbH, Karlsruhe, Germany) with 10% v/v of FBS (fetal bovine serum, Gibco Invitrogen GmbH, Karlsruhe, Germany) and 18 µg/ml of L-proline (Gibco Invitrogen GmbH, Karlsruhe, Germany). On the following day, the cells are charged with 2 µM of Fluo-4 and 0.01% v/v of Pluronic F127 (Molecular Probes Europe BV, Leiden, Netherlands) in HBSS buffer solution (Hank's buffered saline solution, Gibco Invitrogen GmbH, Karlsruhe, Germany) for 30 minutes at 37° C. The plates are then washed three times with HBSS buffer solution and, after incubation for a further 15 minutes at room temperature, used in the FLIPR assay for $Ca^{2+}$ measurement. The $Ca^{2+}$-dependent fluorescence is measured before and after the addition of test substances ($\lambda_{ex}$=488 nm, $\lambda_{em}$=540 nm). Quantification is effected by measuring the highest fluorescence intensity (FC, fluorescence counts) over time.

FLIPR Assay:

The FLIPR protocol consists of two additions of test substance. Test substances (10 µM) are first pipetted onto the cells and the $Ca^{2+}$ influx is compared with the control (capsaicin 10 µM). This gives the percentage activation, based on the $Ca^{2+}$ signal after the addition of 10 µM of capsaicin (CP). After 5 minutes' incubation, 100 nM of capsaicin are applied and the influx of $Ca^{2+}$ is likewise determined. Desensitizing agonists and antagonists lead to suppression of the $Ca^{2+}$ influx. The percentage inhibition compared with the maximum achievable inhibition is calculated using 10 μM of capsaicin. In order to determine the $EC_{50}$ values, the substances are added in various concentrations. Determinations are carried out in triplicate (n=3) and these are repeated in at least three independent experiments (N=4).

2. Analgesic Test Using the Writhing Test on Mice

The analysis of analgesic activity in the compounds of the invention of formula is carried out using the phenylquinone-induced writhing assay in mice, modified as described in the article by I. C. Hendershot and J. Forsaith (1959) in J. Pharmacol. Exp. Ther. 125, 237-240. The relevant description is incorporated herein by reference and is to be regarded as part of the present disclosure.

For the present purpose, male NMRI mice are used having a weight of from 25 to 30 g. Groups of 10 animals per substance dose received, 10 minutes after an intravenous dose of test substances, an intraperitoneal administration of 0.3 ml/mouse of a 0.02% strength aqueous solution of phenylquinone(phenylbenzoquinone, obtainable from Sigma, Deisenhofen; solution produced with the addition of 5% of ethanol and storage in a water bath at 45° C.). The animals were placed individually in observation cages. Using a push-button counter, the number of pain-induced stretching movements (so-called writhing reactions=straightening of the body accompanied by stretching of the rear extremities) was counted over a period of from 5 to 20 minutes following the administration of phenylquinone. The control is provided by animals receiving only physiological saline. All substances were tested using the standard dosage of 10 mg/kg.

The invention will be described in further detail hereinafter with reference to illustrative examples. These explanations are given solely by way of example and do not limit the general inventive concept.

EXAMPLES

The yields of the prepared compounds were not optimized. All temperatures are uncorrected. The term "equivalent" means the equivalent weight of a substance, "RT" means room temperature, "conc." means concentrated, "min" means minutes, "h" means hours, "M" is the concentration stated in mol/ and "aq." means aqueous. Further abbreviations include:

BOP 1-benzotriazolyl-tris-(dimethylamino)-phosphonium
DCM dichloromethane
DMF N,N-dimethylformamide
DIPE diisopropyl ether
EA ethyl acetate The chemicals and solvents used were obtained commercially from conventional suppliers (Acros, Avocado, Aldrich, Bachem, Fluka, Lancaster, Maybridge, Merck, Sigma, TCI, etc.) or were synthesised according to conventional methods known to persons skilled in the art. Silica gel 60 (0.040-0.063 mm) supplied by E. Merck, Darmstadt, was employed as the stationary phase for the column chromatography. The thin-layer chromatography analyses were carried out with HPTLC pre-coated plates, silica gel 60 F 254 supplied by E. Merck, Darmstadt, Germany. The mixing ratios of solvents, mobile phases or for chromatography analyses are always stated in volume/volume. Analysis was effected by mass spectroscopy and NMR spectroscopy.

Example 4 para-tert.-Butyl-trans-N-(4-hydroxy-3-methoxybenzyl)-cinnamic acid amide a) Synthesis of para-tert.-butyl-trans-cinnamic acid 19.20 g (0.185 mol) of malonic acid were dissolved in pyridine (33 ml) and stirred for 15 minutes at RT. 25.00 g (0.154 mmol) of para-tert.-butylbenzaldehyde and 1.50 ml (0.020 mol) of piperidine were then added. The reaction mixture was heated for 8 hours at 100° C., with stirring. After pouring the reaction solution into a mixture of concentrated hydrochloric acid and ice, stirring was continued for a further two hours at room temperature. The resulting precipitate was filtered out with suction. Recrystallisation of the precipitate from methanol yielded 15.20 g (0.074 mol, 48% of theory) of para-tert.-butyl-trans-cinnamic acid.

b) Synthesis of para-tert.-butyl-trans-N-(4-hydroxy-3-methoxybenzyl)-cinnamic acid amide 400 mg (1.96 mmol) of para-tert.-butyl-trans-cinnamic acid were dissolved at 5° C. in DMF (10 ml) together with 290 mg (1.94 mmol) of 4-hydroxy-3-methoxybenzyl-amine hydrochloride and 0.48 ml (6.50 mmol) of triethylamine. After the addition of a solution of 870 mg (1.97 mmol) of BOP in DCM (9 ml), stirring was continued for 16 h at RT. The reaction solution was then poured into water and extracted twice with a mixture of DIPE/EA (1:1). The combined organic phases were washed with 2M eq. hydrochloric acid and three times with 1 M eq. of sodium hydrogen carbonate solution and dried over magnesium sulfate. Follwing removal of the solvents and recrystallisation from DIPE, 384 mg (1.13 mmol, 58% of theoretical) of para-tert.-butyl-trans-N-(4-hydroxy-3-methoxybenzyl)-cinnamic acid amide were obtained.

The following Examples 1 to 3 and 5 to 9 were prepared in a similar manner to the procedure described for Example 4.

1. para-methyl-trans-N-(4-hydroxy-3-methoxybenzyl)-cinnamic acid amide
2. para-ethyl-trans-N-(4-hydroxy-3-methoxybenzyl)-cinnamic acid amide
3. para-isobutyl-trans-N-(4-hydroxy-3-methoxy-benzyl)-cinnamic acid amide
5. para-propyl-trans-N-(4-hydroxy-3-methoxybenzyl)-cinnamic acid amide
6. para-iso-butyl-trans-N-(4-hydroxy-3-methoxybenzyl)-cinnamic acid amide
7. para-neo-pentyl-trans-N-(4-hydroxy-3-methoxybenzyl)-cinnamic acid amide
8. para-butyl-trans-N-(4-hydroxy-3-methoxybenzyl)-cinnamic acid amide
9. para-octyl-trans-N-(4-hydroxy-3-methoxybenzyl)-cinnamic acid amide Pharmacological Data The agonist activity or antagonist activity was determined on human and rat vanilloid receptor 1 (VR1/TRPV1 receptor) using the above-described FLIPR assay. The para-alkyl-substituted N-(4-hydroxy-3-methoxybenzyl)-cinnamic acid amides according to the invention which were examined exhibit an excellent agonist activity on the vanilloid receptor 1 (VR1/TRPV1 receptor). The following Table I shows the pharmacological data for the para-alkyl substituted trans-N-(4-hydroxy-3-methoxybenzyl)-cinnamic acid amides corresponding to formula I:

TABLE I

| Compound of Example | VR1 (Rat) (% Stimulation compared with 10 μM CP) | VR1 (Human) (% Stimulation compared with 10 μM CP) | VR1 (Rat) EC$_{50}$ [nM] | VR1 (Human) EC$_{50}$ [nM] |
|---|---|---|---|---|
| 1 | 92 | 56 | | |
| 2 | 84 | 71 | | |
| 3 | 97 | 71 | | |
| 4 | 106 | 115 | 0.129 ± 0.061 | 0.147 ± 0.043 |
| 5 | 119 | 102 | | |
| 6 | 141 | 103 | | |
| 7 | 142 | 102 | | |
| 8 | 132 | 110 | | |
| 9 | 126 | 97 | | |

The para-alkyl-substituted N-(4-hydroxy-3-methoxybenzyl)-cinnamic acid amides according to the invention corresponding to the foregoing general formula I likewise lead to a marked reduction of nociceptive behavior in the writhing test on mice as described in the following Table II:

TABLE II

| Compound of Example | Dosage [mg/kg] (i.v.) | Reduction of Nociceptive Behavior Relative to Controls [%] |
|---|---|---|
| 2 | 0.1 | 54 |
| 3 | 0.1 | 52 |
| 4 | 0.1 | 63 |
| 5 | 0.316 | 55 |
| 6 | 0.1 | 70 |
| 9 | 0.1 | 47 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A para-Alkyl-substituted N-(4-hydroxy-3-methoxybenzyl)-cinnamic acid amide compound corresponding to formula I:

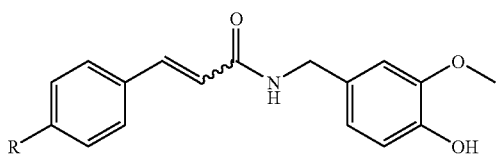

I wherein R represents a linear or branched alkyl group;
or a pharmaceutically acceptable salt thereof;
in the form of a pure isomer or a mixture of isomers in any mixing ratio.

2. A compound according to claim 1, wherein said compound is in the form of a pure isomer.

3. A compound according to claim 1, wherein said compound is in the form of a mixture of isomers.

4. A compound according to claim 1, wherein said compound is a trans isomer corresponding to formula Ia:

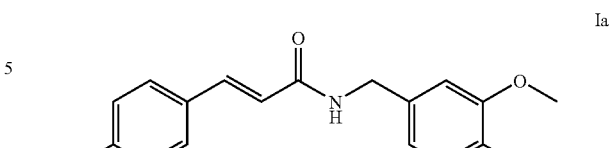

Ia wherein R represents a linear or branched alkyl group;
or a pharmaceutically acceptable salt thereof;
in the form of a pure isomer or a mixture of isomers in any mixing ratio.

5. A compound according to claim 1, wherein R represents a linear or branched C$_{1-20}$ alkyl group.

6. A compound according to claim 5, wherein R represents a linear or branched C$_{1-10}$ alkyl group.

7. A compound according to claim 6, wherein R represents an alkyl group selected from the group consisting of methyl; ethyl; n-propyl; isopropyl; n-butyl; isobutyl; sec.-butyl; tert.-butyl; n-pentyl; 2-pentyl; 3-pentyl; isopentyl; neopentyl; 1,1-dimethylpropyl; 1,2-dimethylpropyl; n-hexyl; 2-hexyl; 3-hexyl; isohexyl; neohexyl; n-heptyl; 2-heptyl; 3-heptyl; 4-heptyl; isoheptyl; neoheptyl; n-octyl; 2-octyl; 3-octyl; 4-octyl; isooctyl; neooctyl; n-nonyl; 2-nonyl; 3-nonyl; 4-nonyl; 5-nonyl; isononyl; neononyl, and n-decyl.

8. A compound according to claim 7, wherein R represents an alkyl group selected from the group consisting of methyl; ethyl; n-propyl; isopropyl; n-butyl; isobutyl; tert.-butyl; neopentyl, and n-octyl.

9. A compound according to claim 1, selected from the group consisting of:
para-methyl-trans-N-(4-hydroxy-3-methoxy-benzyl)-cinnamic acid amide;
para-ethyl-trans-N-(4-hydroxy-3-methoxy-benzyl)-cinnamic acid amide;
para-isopropyl-trans-N-(4-hydroxy-3-methoxy-benzyl)-cinnamic acid amide;
para-tert.-butyl-trans-N-(4-hydroxy-3-methoxy-benzyl)-cinnamic acid amide;
para-propyl-trans-N-(4-hydroxy-3-methoxybenzyl)-cinnamic acid amide;
para-isobutyl-trans-N-(4-hydroxy-3-methoxybenzyl)-cinnamic acid amide;
para-neopentyl-trans-N-(4-hydroxy-3-methoxybenzyl)-cinnamic acid amide;
para-butyl-trans-N-(4-hydroxy-3-methoxybenzyl)-cinnamic acid amide; and
para-octyl-trans-N-(4-hydroxy-3-methoxybenzyl)-cinnamic acid amide;
or a pharmaceutically acceptable salt thereof.

10. A compound according to claim 9, wherein said compound is para-tert.-butyl-trans-N-(4-hydroxy-3-methoxy-benzyl)-cinnamic acid amide, or a pharmaceutically acceptable salt thereof.

11. A process for preparing a compound according to claim 1, said process comprising:
reacting an aldehyde of formula II

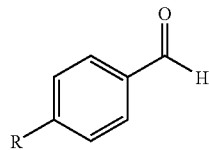

wherein R has the meaning given in claim 1,
in the presence of a base with malonic acid, optionally in a reaction medium, to obtain a para-alkyl-substituted cinnamic acid of formula III

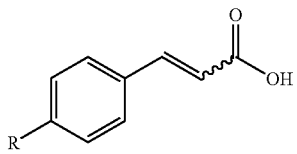

or salt thereof, wherein R has the meaning stated above; optionally isolating or purifying the compound of formula III or salt thereof;

then reacting the compound of formula III or salt thereof with 4-hydroxy-3-methoxybenzylamine or a salt thereof in the presence of a base in a reaction medium, and optionally in the presence of a coupling agent, to give a corresponding compound of formula I

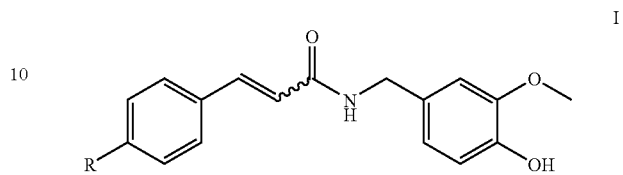

or salt thereof, wherein R has the meanings stated above, and optionally purifying or isolating the compound of formula I.

12. A pharmaceutical composition comprising a compound according to claim 1, and at least one physiologically acceptable carrier or adjuvant.

13. A method of treating or inhibiting pain in a patient in need thereof, said method comprising administering to said patient a pharmacologically effective amount of a compound according to claim 1.

* * * * *